United States Patent
Nagata et al.

(10) Patent No.: US 8,739,397 B2
(45) Date of Patent: Jun. 3, 2014

(54) ELECTRODE SHEET AND PROCESS FOR PRODUCING ELECTRODE SHEET

(75) Inventors: Shinya Nagata, Osaka (JP); Nobumichi Iwasaki, Gunma (JP)

(73) Assignees: Nihon Kohden Corporation, Tokyo (JP); Asakura Senpu Co., Ltd., Kiryu-Shi Gunma (JP)

( * ) Notice: Subject to any disclaimer, the term of this patent is extended or adjusted under 35 U.S.C. 154(b) by 404 days.

(21) Appl. No.: 12/679,747

(22) PCT Filed: Sep. 25, 2008

(86) PCT No.: PCT/JP2008/067293
§ 371 (c)(1),
(2), (4) Date: Mar. 24, 2010

(87) PCT Pub. No.: WO2009/041496
PCT Pub. Date: Apr. 2, 2009

(65) Prior Publication Data
US 2010/0198038 A1 Aug. 5, 2010

(30) Foreign Application Priority Data
Sep. 25, 2007 (JP) .................. 2007-247960

(51) Int. Cl.
*A61B 5/0408* (2006.01)
*H05K 3/12* (2006.01)
*B32B 27/12* (2006.01)

(52) U.S. Cl.
USPC ............. 29/829; 600/509; 600/395; 600/388; 442/110

(58) Field of Classification Search
USPC ......... 600/388, 389, 395, 509; 29/825, 592.1, 29/829; 442/117
See application file for complete search history.

(56) References Cited

U.S. PATENT DOCUMENTS

| | | | |
|---|---|---|---|
| 4,353,372 A | | 10/1982 | Ayer |
| 4,365,634 A | * | 12/1982 | Bare et al. ............... 600/391 |
| 5,865,740 A | * | 2/1999 | Kelly et al. ............... 600/382 |
| 6,385,473 B1 | * | 5/2002 | Haines et al. ............. 600/393 |
| 7,468,332 B2 | * | 12/2008 | Avloni ...................... 442/64 |

(Continued)

FOREIGN PATENT DOCUMENTS

| | | |
|---|---|---|
| CN | 1708328 | 12/2005 |
| CN | 1970657 | 5/2007 |

(Continued)

OTHER PUBLICATIONS

Kordas et al. "Inkjet Printing of Electrically Conductive Patterns of Carbon Nanotubes" Small 2006, 2, No. 8-9; pp. 1021-1025 (2006).*
ScienceDaily "Nanotube Ink: Desktop Printing of Carbon Nanotube Patterns" Aug. 31, 2006; available at http://www.sciencedaily.com/releases/2006/08/060830220023.htm.*

(Continued)

*Primary Examiner* — Lee S Cohen
*Assistant Examiner* — Erin M Cardinal
(74) *Attorney, Agent, or Firm* — Jason H. Vick; Sheridan Ross, PC

(57) ABSTRACT

A material 2 is used as the fabric of a shirt, and formed by knitting a blended yarn of polyester and urethane. The material 2 is flattened by a calendering process. A conductive ink is printed on an insulating layer serving as an underlayer to form wiring layers L1 to L10. The conductive ink contains carbon nanotubes. Consequently, wiring layers that ensure a sufficient conductivity can be obtained.

9 Claims, 11 Drawing Sheets

(56) References Cited

U.S. PATENT DOCUMENTS

| | | | |
|---|---|---|---|
| 2004/0054276 A1* | 3/2004 | Finneran et al. | 600/393 |
| 2004/0138546 A1* | 7/2004 | Reho et al. | 600/382 |
| 2005/0106977 A1* | 5/2005 | Coulston | 442/301 |
| 2005/0229328 A1* | 10/2005 | Tran | 8/115.51 |
| 2005/0239075 A1 | 10/2005 | Yanagidaira et al. | |
| 2006/0247509 A1 | 11/2006 | Tuccillo et al. | |
| 2007/0078324 A1* | 4/2007 | Wijisiriwardana | 600/386 |
| 2007/0276273 A1* | 11/2007 | Watson, Jr | 600/511 |
| 2007/0285868 A1* | 12/2007 | Lindberg et al. | 361/232 |
| 2007/0293750 A1* | 12/2007 | Kuo et al. | 600/388 |
| 2008/0014528 A1* | 1/2008 | Bailey et al. | 430/200 |
| 2008/0044651 A1* | 2/2008 | Douglas | 428/339 |
| 2010/0234715 A1* | 9/2010 | Shin et al. | 600/388 |

FOREIGN PATENT DOCUMENTS

| | | |
|---|---|---|
| JP | 1990-051506 U | 4/1990 |
| JP | 1991-000707 U | 1/1991 |
| JP | 1992-108168 A | 4/1992 |
| JP | 1994-007324 A | 1/1994 |
| JP | 1995-007196 U | 1/1995 |
| JP | 1997-131328 A | 5/1997 |
| JP | 10-211179 A | 8/1998 |
| JP | 1999-172559 A | 6/1999 |
| JP | 2000-328303 A | 11/2000 |
| JP | 2002-159458 A | 6/2002 |
| JP | 2004-532937 A | 10/2004 |
| JP | 2005-205223 A | 8/2005 |
| JP | 2005-285519 A | 10/2005 |
| JP | 2006-122415 A | 5/2006 |
| WO | WO 02/055769 | 7/2002 |
| WO | WO 03/072185 | 9/2003 |
| WO | WO 2005/089642 A1 | 9/2005 |
| WO | WO 2005/119772 | 12/2005 |
| WO | WO 2007/066513 A1 | 6/2007 |
| WO | WO 2008/092098 | 7/2008 |

OTHER PUBLICATIONS

Shim et al. "Smart Electronic Yarns and Wearable Fabrics for Human Biomonitoring made by Carbon Nanotube Coating with Polyelectrolytes" Nano Letters: 8(12), pp. 4151-4157 (2008).*

Suzuki et al. "Carbon Nanotubes on Carbon Fabrics for Flexible Field Emitter Arrays" Applied Physics Letters: 93, 053107 (2008).*

International Search Report prepared by the Japanese Patent Office on Dec. 22, 2008, for International Application No. PCT/JP2008/067293.

Supplementary European Search Report for corresponding European Application No. 08833687.0, issued Jan. 19, 2012, 6 pages.

Written Opinion (including English translation) for International (PCT) Patent Application No. PCT/US2008/067293, issued Mar. 25, 2010.

International Preliminary Report on Patentability (including English translation) for International (PCT) Patent Application No. PCT/US2008/067293, issued Mar. 30, 2010.

First Official Action (including translation) for corresponding Chinese Patent Application No. 200880108402.6, issued Apr. 25, 2011, 21 pages.

Rejection Decision (including translation) for corresponding Chinese Patent Application No. 200880108402.6, issued Oct. 20, 2011, 20 pages.

Third Notification of Office Action (including translation) for corresponding Chinese Patent Application No. 200880108402.6, issued Nov. 5, 2012, 6 pages.

Notification of Reasons for Refusal (including translation) for Japanese Patent Application No. 2009-534355, mailed Nov. 5, 2012, 4 pages.

Second Notification of Office Action (including translation) for corresponding Chinese Patent Application No. 200880108402.6, issued Jul. 4, 2012, 7 pages.

Official Action for corresponding European Application No. 08833687.0, issued Jul. 30, 2012, 3 pages.

Official Action for corresponding European Application No. 08833687.0, issued Jul. 9, 2013, 4 pages.

* cited by examiner

ELECTRODE SHEET AND PROCESS FOR PRODUCING ELECTRODE SHEET

CROSS REFERENCE TO RELATED APPLICATIONS

This application is a national stage application under 35 U.S.C. 371 of PCT application No. PCT/JP2008/067293 having an international filing date of 25 Sep. 2008, which designated the United States, which PCT application claimed the benefit of Japanese Application No. 2007-247960 filed 25 Sep. 2007, the entire disclosure of each of which is hereby incorporated herein by reference.

TECHNICAL FIELD

The present invention relates to an electrode for use to measure an electrocardiographic waveform or the like, and in particular to the improvement of wiring for an electrode and so forth.

BACKGROUND ART

Biological information including an electrocardiogram is occasionally measured in emergencies such as in an ambulance. A measuring person attaches an electrode to each of the chest, wrists, and ankles of a person to be measured by suction, and then takes an electrocardiogram using an electrocardiogram measurement device. The electrocardiogram measurement according to the prior art requires much time to attach electrodes by suction, and thus may not be suitable for use in emergencies. In addition, a large number of wiring cords which are connected to a large number of electrodes are occasionally tangled with each other to lower the working efficiency.

In order to address such issues, Patent Document 1 discloses a technique in which electrodes are provided to a garment such as a T-shirt.

Patent Document 2 discloses a technique in which a metal layer is provided on a surface of a fabric by plating or vapor deposition to maintain the conductivity of a wiring layer provided on the fabric to be high.

Patent Document 1: JP-A-2002-159458

Patent Document 2: JP-A-1992(Hei4)-108168

DISCLOSURE OF THE INVENTION

Problem to be Solved by the Invention

While the prior art according to Patent Document 1 above facilitates mounting of the electrodes, however, the conductivity of wiring provided on a fabric is low.

While Patent Document 2 successfully addresses the above issues, providing a metal layer on a surface of a fabric by plating or vapor deposition is not easy and complicates the production process.

Moreover, the composition of a conductive ink to be printed on a surface of a fabric, which has significant projections and depressions, is particularly discussed in neither of the above prior art documents.

In view of the foregoing, it is therefore an object of the present invention to provide an electrode that ensures the conductivity of a wiring layer.

Means for Solving the Problem

Several aspects of the present invention are as follows.

(1) According to the present invention, an electrode sheet includes: a material with a flattened surface; a wiring layer provided on the flattened surface of the material and formed of a conductive ink containing carbon nanotubes; and an electrode connected to the wiring layer.

Thus, it is possible to ensure a sufficient conductivity, and to measure biological information quickly and accurately.

(2) In the electrode sheet according to the present invention, the conductive ink comprise a binder containing an acrylic resin, a dispersant containing an acrylic acid polymer, and carbon nanotubes.

(3) In the electrode sheet according to the present invention, the material is formed by knitting one of a blended yarn of polyester fibers and urethane fibers, a yarn of nylon fibers, and a yarn of urethane fibers.

Thus, it is possible to obtain a flattened and yet flexible material.

(4) In the electrode sheet according to the present invention, surface flattening is carried out on the material by a calendering process.

Thus, it is possible to flatten the material by a calendering process.

(5) In the electrode sheet according to the present invention, a lower insulating layer is provided on the flattened surface of the material, and the wiring layer may be formed on the lower insulating layer.

Thus, by using the lower insulating layer as an underlayer for the wiring layer, it is possible to form the wiring layer on a flatter surface, and to ensure the conductivity.

(6) In the electrode sheet according to the present invention, an upper insulating layer is formed on the wiring layer.

Thus, it is possible to prevent any conductive portion other than the electrode from contacting a human body, and to prevent erroneous measurements.

(7) In the electrode sheet according to the present invention, the electrode is formed of an adhesive conductive paste.

Thus, it is possible to secure the electrode sheet to a human body with the electrode itself.

(8) In the electrode sheet according to the present invention, the electrode is an electrode that measures an electrocardiographic waveform of a subject with a garment.

Thus, it is possible to take an electrocardiogram quickly.

(9) The electrode sheet according to the present invention further comprises: a connector that is connectable to an external device; and a film substrate having a wire connected to the connector, in which the wire of the film substrate is electrically connected and physically secured to the wiring layer.

Thus, it is possible to connect an external device easily and quickly.

(19) According to the present invention, an electrode sheet comprises: a flexible material; a wiring layer provided on a flattened surface of the material and formed of a conductive ink containing carbon nanotubes; and an electrode connected to the wiring layer.

(20) According to the present invention, a garment comprises: a material with a flattened surface; and a wiring layer provided on the flattened surface of the material and formed of a conductive ink containing carbon nanotubes.

Thus, it is possible to ensure a sufficient conductivity, and to transfer biological information accurately.

(21) The garment according to the present invention further comprises an electrode connected to the wiring layer.

Thus, it is possible to ensure a sufficient conductivity, and to measure biological information quickly and accurately.

In the context of the present invention, the term "electrode sheet" refers to a sheet having an electrode that measures biological information such as an electrocardiogram, an electromyogram, and an electroencephalogram, and that may include not only sheets having a flat shape but also those having a three-dimensional shape that conforms to the shape of a body and those having a ring shape.

The term "material" refers to a carrier that is provided with an electrode and a wiring layer, and that may include not only woven or knit materials but also thin flexible sheets made of rubber, plastic, or the like.

DESCRIPTION OF REFERENCE SYMBOLS

Figure 1:
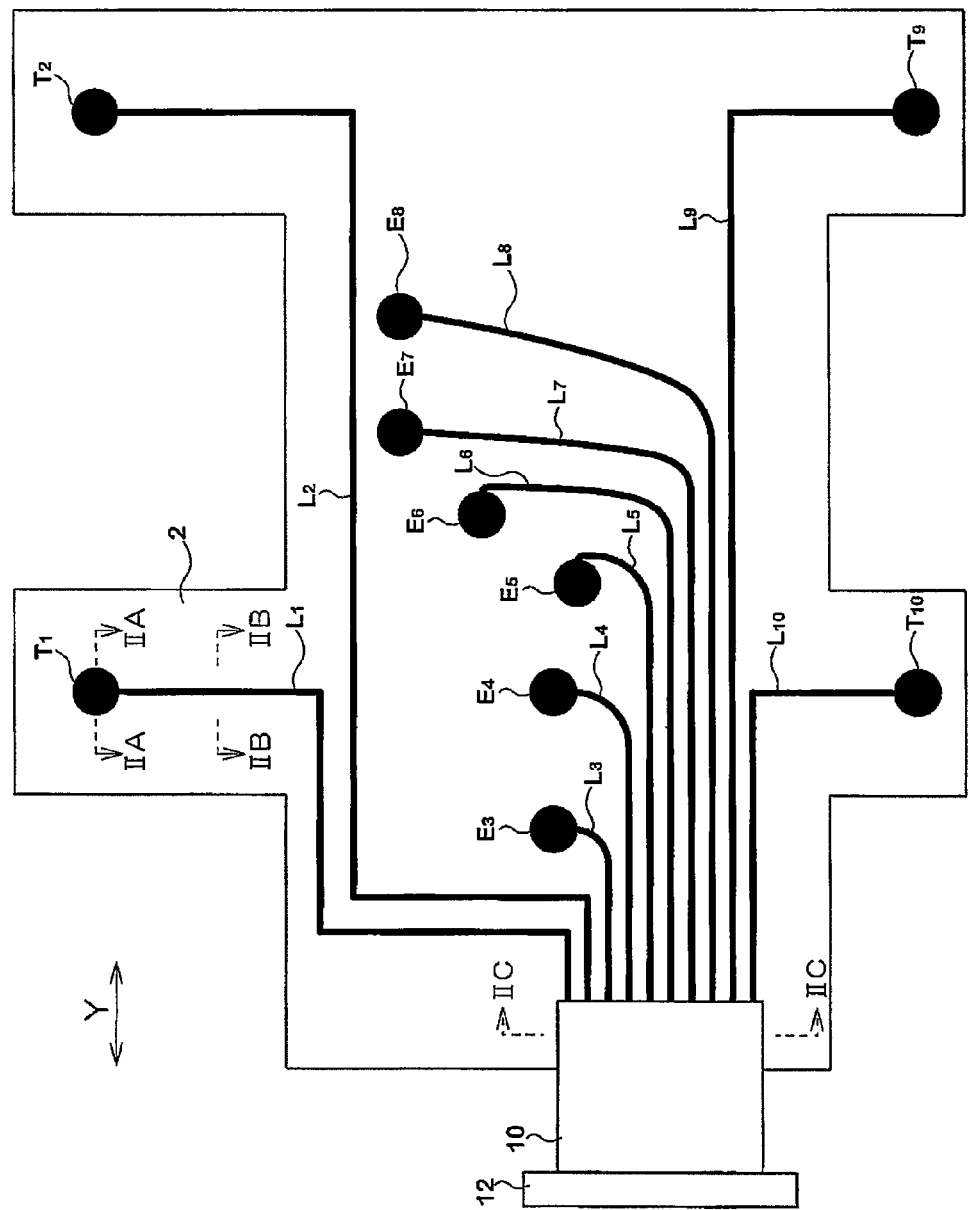
FIG. 1 shows the appearance of an electrode sheet according to an embodiment of the present invention.

2: material
T1, T2, T9, T10: neutral electrode
E3, E4, E5, E6, E7, E8: chest electrode
L1 to L10: wiring layer
Embodiments for Carrying Out the Invention
1. Configuration FIG. 1 shows the appearance of an electrode sheet 1 for electrocardiogram measurement according to an embodiment of the present invention. As shown in the drawing, chest electrodes E3, E4, . . . , E8, neutral electrodes T1, T2, T9, T10, and wiring layers L1, L2, . . . , L10 are formed on a material 2. The chest electrodes E3, E4, . . . , E8 and the neutral electrodes T1, T2, T9, and T10 for electrocardiogram measurement are formed of an adhesive conductive paste.

Figure 2A:
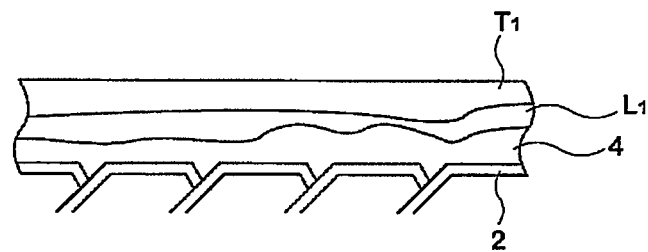
FIG. 2 shows a cross-sectional view of various portions of FIG. 1.

FIG. 2A shows a cross-sectional view taken along the line IIA-IIA of FIG. 1. A lower insulating layer 4 made from an insulating ink is formed on the material 2, and the wiring layer L1 made from a conductive ink is formed on the lower insulating layer 4. The neutral electrode T1 is formed on the wiring layer L1. The other electrode portions are configured in the same manner.

The material 2 is preferably formed by knitting to provide elasticity. The insulating ink forming the lower insulating layer 4 is made from an acrylic material. The conductive ink forming the wiring layer L1 is obtained by mixing carbon nanotubes (5% to 10% by weight), a dispersant, and a binder. The conductive paste forming the chest electrodes E3, E4, . . . , E8 and the neutral electrodes T1, T2, T9, and T10 is made from silver/silver chloride (ST-gel, manufactured by Sekisui Plastics Co., Ltd.).

A conductive ink containing carbon nanotubes is used because it keeps providing conductivity to the wiring layer with the elongated carbon nanotubes tangled with each other even when the material is stretched. From this point of view, the carbon nanotubes are preferably long. In consideration of ease of manufacture, the carbon nanotubes are preferably 80 μm to 150 μm long. More preferably, the carbon nanotubes are 100 μm to 120 μm long. While single-layer carbon nanotubes may be used, multi-layer carbon nanotubes are preferably used in consideration of conductivity. While the single-layer carbon nanotubes generally have a diameter of 0.5 nm to 5 nm, the multi-layer carbon nanotubes generally have a diameter of 10 nm to 100 nm. In the embodiment, multi-layer carbon nanotubes manufactured by an arc discharge method are used.

The carbon nanotubes are highly cohesive. Thus, a dispersant is used to disperse the carbon nanotubes as uniformly as possible. In the embodiment, an acrylic acid polymer (for example, a polymer of acrylic acid and amide acrylate) is used as the dispersant. Other examples of the dispersant include a nonionic polymer surfactant (for example, a polyester type, a Pluronic type, a tetranic type, an acrylic type, and so forth).

A binder composed of a flexible material is used to organize the carbon nanotubes in a certain form so that it keeps them in shape to a certain degree even in the case where the material is stretched or shrunk. In the embodiment, a binder containing an acrylic resin (for example, a polymer or a copolymer containing one of methacrylic ester, acrylic ester, and ethyl acrylate as the main component) is used. Other examples of the binder include a polyester resin, a urethane resin, or a silicone resin.

Figure 2B:
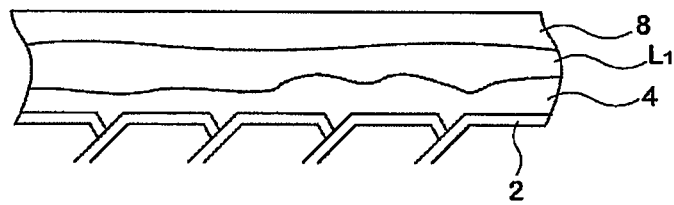

FIG. 2B shows a cross-sectional view taken along the line IIB-IIB of FIG. 1. FIG. 2B is the same as FIG. 2A in that the lower insulating layer 4 made from an insulating ink is formed on the material 2, and the wiring layer L1 made from a conductive ink is formed on the lower insulating layer 4. An upper insulating layer 8 made from an insulating ink is formed on the wiring layer L1. The other wiring layers are structured in the same manner.

The upper insulating layer 8 covers the wiring layers L1, L2, . . . , L10 so that no conductive portions other than the chest electrodes E3, E4, . . . , E8 and the neutral electrodes T1, T2, T9, and T10 contact a human body. This enables accurate measurement of an electrocardiogram.

Figure 2C:
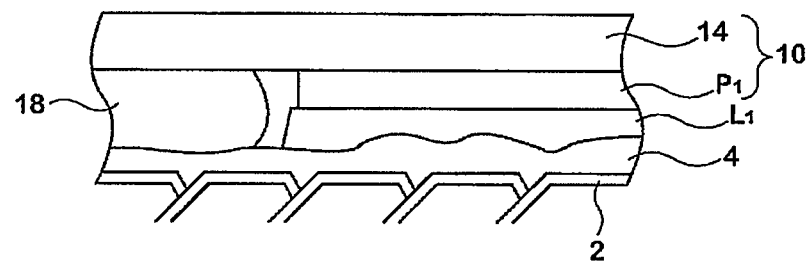

A connector 12 is connected to an end of the material 2 via a film substrate 10. FIG. 2C shows a partial cross-sectional view taken along the line IIC-IIC of FIG. 1. The lower insulating layer 4 made from an insulating ink is formed on the material 2, and the wiring layers L1, L2, . . . , L10 made from a conductive ink are selectively formed on the lower insulating layer 4. Meanwhile, the film substrate 10 is formed by printed wires P1, P2, . . . , P10 on an insulating flexible film 14. The wires P1, P2, . . . , P10 are respectively provided at positions corresponding to the wiring layers L1, L2, . . . , L10. The film substrate 10 and the material 2 are secured to each other by an adhesive 18 with each of the wires P1, P2, . . . , P10 of the film substrate 10 contacting the corresponding one of the wiring layers L1, L2, . . . , L10. The insulating adhesive 18 is provided at portions other than the wires P1, P2, . . . , P10 and the wiring layers L1, L2, . . . , L10.

The film substrate 10 is provided with the connector 12 that is connectable to an external device (such as an electrocardiograph).

In the electrocardiogram measurement, the contact resistance between the skin of a human body and the electrodes can be about several MΩ. Thus, a resistance value, from one end (electrode portion) of the wiring layer to the other end (connector portion), of 1000 KΩ or less is sufficient for practical use when the material is stretched by about 30%. The resistance value is preferably 100 KΩ, more preferably 10 KΩ.

2. Method of Use

Figure 3:
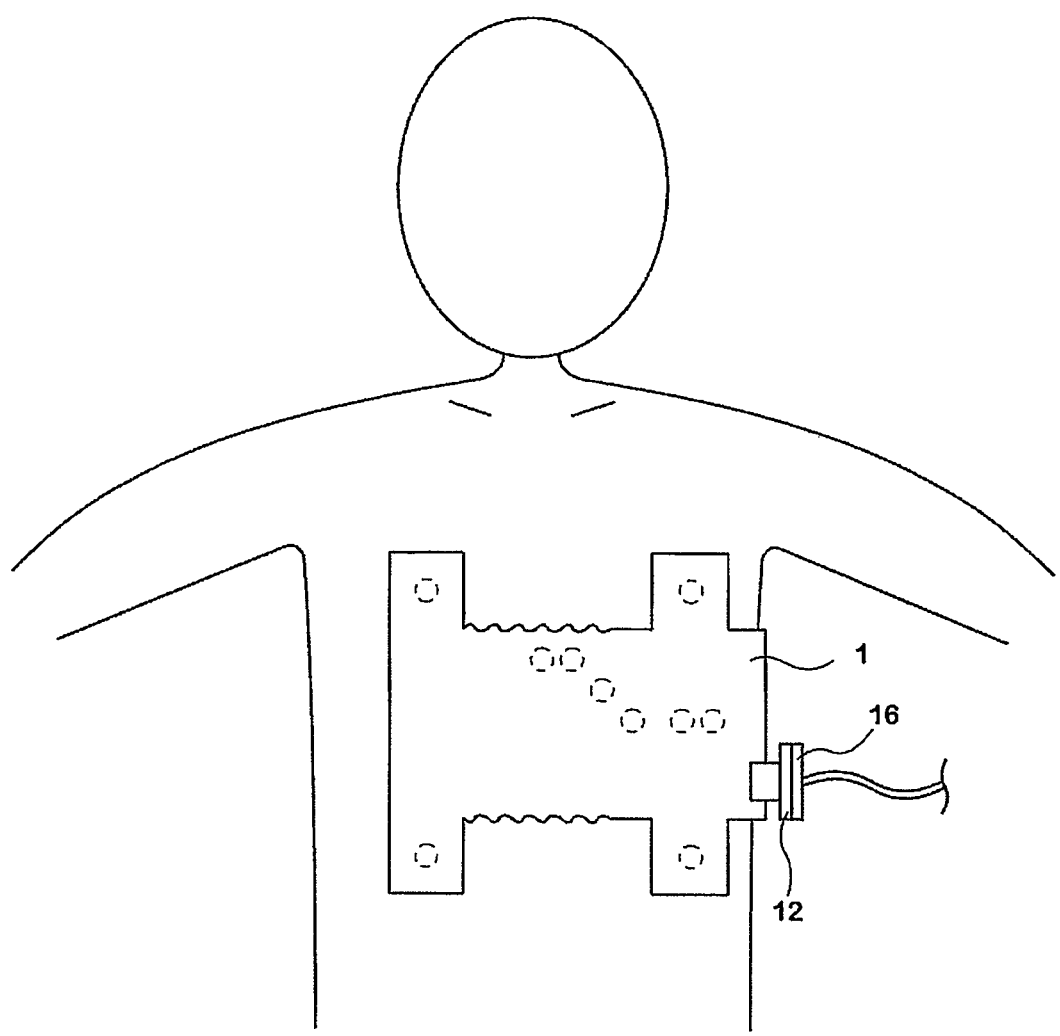
FIG. 3 shows the electrode sheet in use.

As shown in FIG. 3, the electrode sheet 1 is used with the chest electrodes E3, E4, . . . , E8 and the neutral electrodes T1, T2, T9, and T10 ticking to a human body. Each of the electrodes is formed of an adhesive conductive paste to be suitable for sticking. The material 2 may be slackened or stretched to dispose each of the electrodes at a desired position.

A device-side connector 16 that is connectable to an electrocardiograph is connected to the connector 12. This allows measurement of an electrocardiogram with the electrocardiograph.

The use of the electrode sheet eliminates the risk that the wires from the electrodes are tangled with each other, and allows quick preparation for measurement with the electrodes roughly disposed in position previously.

3. Method of Manufacture 3.1 Material

In the embodiment, a blended yarn of polyester and urethane is used as the fibers of the shirt. A blended yarn with about one fifth (preferably 18%) of urethane with respect to polyester is used. Such a yarn is knit to form the material of the shirt. Urethane which has high elasticity itself is knit to obtain much higher elasticity.

Any natural or synthetic fibers other than those described above may be used as the fibers of the shirt. For example, materials obtained by knitting or weaving non-blended polyester, non-blended urethane, non-blended nylon, non-blended cotton, non-blended acryl, or a blended yarn of these may be used. Moreover, materials obtained by knitting or weaving various natural fibers such as cotton and wool may also be used. These fibers may be blended at any proportion to obtain the material.

While a knit material is preferable where the elasticity is important, a woven material or a nonwoven material may also be used.

3.2 Presetting

The above material is heated at around 200 degrees Celsius (for example, 196 degrees Celsius). This eliminates distortion to stabilize the shape of the material.

3.3 Dyeing

Next, the material is immersed in a hot dye solution to dye the material. In the case where it is not necessary to dye the material, the process may be omitted.

3.4 Finishing

The material is heated again at around 170 degrees (for example, 160 degrees) Celsius to adjust the dimensions.

3.5 Calendering Process

Subsequently, a surface of the material is subjected to a smoothing process. Smoothing refers to a process in which projections and depressions formed by loops on a surface of the material are flattened using heat or pressure to smooth the surface compared to that before the process. In the embodiment, smoothing is performed using a calendering process.

Figure 4A:
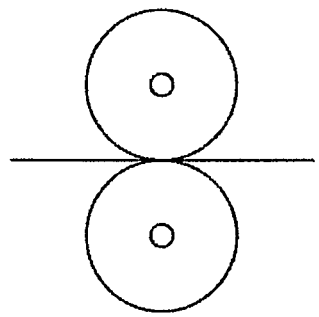
FIG. 4 shows the structure of a calendering machine.
Figure 4B:
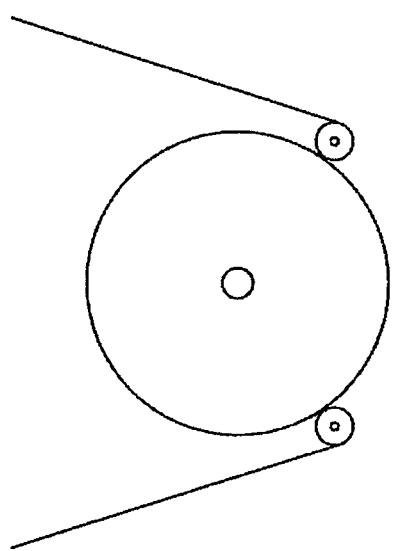
Figure 5A:
FIG. 5 shows a surface of a material before and after a calendering process.
Figure 5B:

For example, calendering machines as shown in FIGS. 4A and 4B may be used. A material with a width of 100 to 220 cm is subjected to a linear pressure of 20 tons to 50 tons using rollers at temperatures of 190 to 200 degrees Celsius. As a result, the surface of the material changes from a state with significant projections and depressions as shown in FIG. 5A into a relatively flat state as shown in FIG. 5B.

3.6 Shield Printing

After the calendering process, the lower insulating layer 4 is printed with an insulating ink as an underlayer for each of the wiring layers L1, L2, . . . , L10. An acrylic resin (for example, a binder EN-ME/EN-MRE manufactured by Matsui Shikiso Chemical Co., Ltd.) is used as the insulating ink. However, a urethane resin or the like may also be used.

The lower insulating layer 4 is wider than each of the wiring layers L1, L2, . . . , L10 by 1 mm to several mm. This allows each of the wiring layers L1, L2, . . . , L10 to be placed on the lower insulating layer 4 even if the wiring layers L1, L2, . . . , L10 are printed in a displaced manner.

3.7 Wiring Printing

Next, the wiring layers L1, L2, . . . , L10 are printed on the lower insulating layer 4. The conductive ink for the wiring layers L1, L2, . . . , L10 is obtained by compounding carbon nanotubes, a dispersant, and a binder. An amphipathic acrylic polymer (a polymer of acrylic acid and amide acrylate, which may be TX-17-100 manufactured by Kyoeisha Chemical Co., Ltd., for example) is used as the dispersant. An acrylic soft binder (a polymer of acrylic ester, which may be Light Epoch T-23M manufactured by Kyoeisha Chemical Co., Ltd., for example) is used as the binder. The compounding ratios of the amphipathic acrylic polymer, the acrylic soft binder, and the carbon nanotubes are respectively 0.5 to 2.0% by weight, 5 to 10% by weight, with the remaining component being water.

Increasing the compounding ratio of the carbon nanotubes improves the conductivity. However, a compounding ratio of the carbon nanotubes exceeding 10% by weight reduces the flexibility of the wiring layers to result in unfavorable cracking of the wiring layers.

Tables 1 and 2 show variations in conductivity with the carbon nanotubes compounded at various ratios. Table 1 corresponds to a case where printing is performed on the front surface of the material. Table 2 corresponds to a case where printing is performed on the back surface of the material. In the tables, TX17-1 and TX17-1A are obtained by compounding 0.85% by weight of the amphipathic acrylic polymer (dispersant), 5.8% by weight of the acrylic soft binder, and 5.0% of the carbon nanotubes. In the example, multi-layer carbon nanotubes with a diameter of 150 nm and a length of 10 to 20 μm are used as the carbon nanotubes. TX17-1B is obtained by compounding 1.6% by weight of the amphipathic acrylic polymer (dispersant), 7.2% by weight of the acrylic soft binder, and 8.3% of the carbon nanotubes. TX17-1C is obtained by compounding 1.7% by weight of the amphipathic acrylic polymer (dispersant), 5.6% by weight of the acrylic soft binder, and 8.9% of the carbon nanotubes.

TABLE 1

Electrical resistance for all terminals printed on front surface

| Material number: 335 (not calendered) | | Material number: A0127SL (calendered) | | |
| --- | --- | --- | --- | --- |
| CNT concentration (%) 5.0 | | 5.0 | 8.3 | 8.9 |
| TX17-1 electrical resistance (kΩ) | Terminal | TX17-1A Electrical resistance (kΩ) | TX17-1B Electrical resistance (kΩ) | TX17-1C Electrical resistance (kΩ) |
| 300 | A | 200 | 55 | 55 |
| 200 | B | 250 | 60 | 36 |
| 300 | C | 150 | 28 | 22 |
| 300 | D | 150 | 40 | 34 |
| 350 | E | 250 | 42 | 34 |
| 350 | F | 250 | 45 | 40 |
| 350 | G | 200 | 45 | 55 |
| 300 | H | 200 | 50 | 32 |

TABLE 1-continued

Electrical resistance for all terminals printed on front surface

|         | 500   | I | 400   | 100  | 90   |
|---------|-------|---|-------|------|------|
|         | 400   | J | 400   | 70   | 70   |
| Average | 335.0 |   | 245.0 | 53.5 | 46.8 |

TABLE 2

Electrical resistance for wiring layers printed on back surface

| Material number: 335 (not calendered) | | | Material number: A0127SL (calendered) | | |
|---|---|---|---|---|---|
| CNT concentration (%) | 5.0 | | 5.0 | 8.3 | 8.9 |
| TX17-1 electrical resistance (kΩ) | | Terminal | TX17-1A Electrical resistance (kΩ) | TX17-1B Electrical resistance (kΩ) | TX17-1C Electrical resistance (kΩ) |
| | 500 or more | A | 105 | 55 | 40 |
| | 500 or more | B | 105 | 45 | 36 |
| | 500 or more | C | 100 | 25 | 20 |
| | 500 or more | D | 100 | 45 | 40 |
| | 500 or more | E | 105 | 60 | 40 |
| | 500 or more | F | 105 | 60 | 35 |
| | 500 or more | G | 105 | 60 | 37 |
| | 500 or more | H | 100 | 37 | 19 |
| | 500 or more | I | 250 | 100 | 75 |
| | 500 or more | J | 200 | 75 | 75 |
| Average | 500 or more | | 127.5 | 56.2 | 41.7 |

The conductive ink may include other conductive materials or ink such as silver particles in addition to or in place of the carbon nanotubes.

3.8 Shield Printing

Next, the upper insulating layer 8 is printed with an insulating ink on each of the wiring layers L1, L2, ..., L10. The material of the insulating ink used to form the upper insulating layer is the same as the material of the insulating ink used to form the lower insulating layer. The upper insulating layer 8 is formed to be wider than each of the wiring layers L1, L2, ..., L10 by 1 mm to several mm so as to reliably cover each of the wiring layers L1, L2, ..., L10 even if printing is performed in a more or less displaced manner.

The upper insulating layer 8 is not printed on portions at which the chest electrodes E3, E4, ..., E8 and the neutral electrodes T1, T2, T9, and T10 are to be formed and on a portion to which the film substrate 10 is to be jointed.

3.9 Hot-melt Printing

Figure 6:
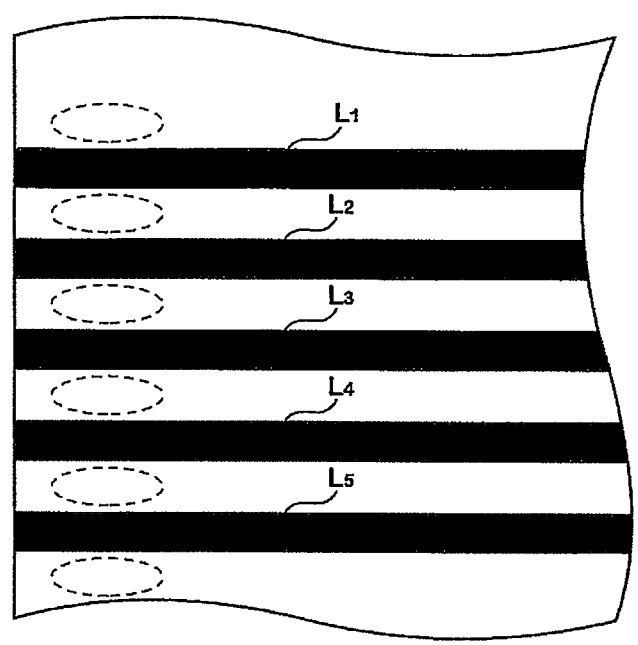
FIG. 6 shows a portion of the electrode sheet that is joined to a film substrate.

Next, a hot-melt adhesive is printed to join the wiring layers L1, L2, ..., L10 to the film substrate 10. In this event, as shown in FIG. 6, the hot-melt adhesive is printed at portions in the vicinity of the wiring layers L1, L2, ..., L10 and not on the wiring layers L1, L2, ..., L10. A mixture of an acrylic ester copolymer resin, ethylene glycol, water, and so forth (for example, a binder K-2050 manufactured by Meisei Chemical Works, Ltd.) is used as the hot-melt adhesive.

While the upper insulating layer 8, the wiring layers L, the lower insulating layer 4, and the hot-melt adhesive are printed using hand printing in the embodiment, they may be printed using automatic printing, rotary printing, inkjet printing, or the like.

3.10 Finishing

Next, the entire material 2 is heated at about 150 degrees Celsius to promote curing of the upper insulating layer 8 for sufficient insulation.

3.11 Pasting of Conductive Paste

A conductive paste is pasted on electrode portions of the wiring layers L1, L2, ..., L10. Silver/silver chloride (ST-gel, manufactured by Sekisui Plastics Co., Ltd.) may be used as the conductive paste.

3.12 Film Adhesion

Figure 7:
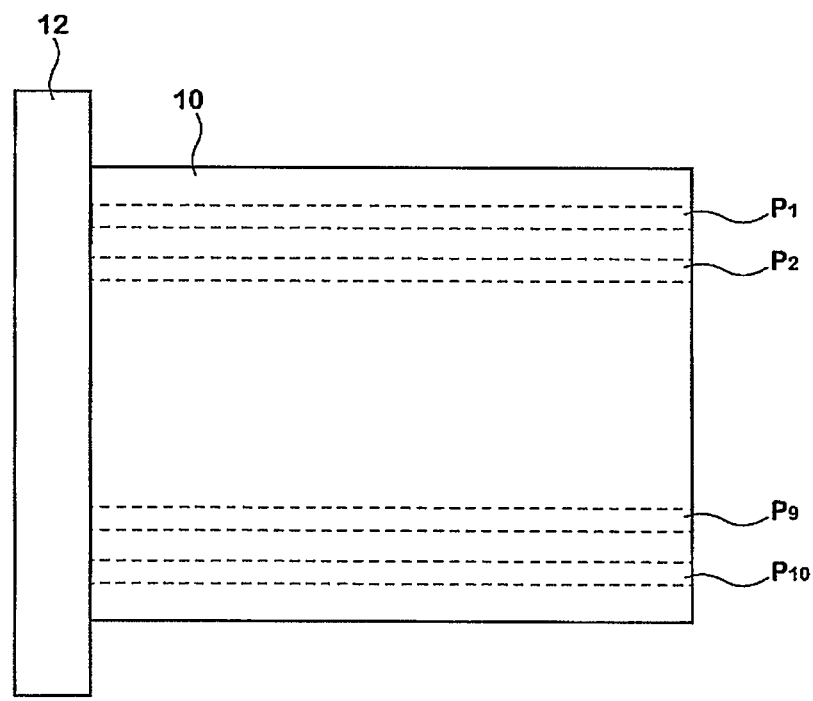
FIG. 7 shows the film substrate and a connector.

The film substrate 10 with the connector 12 shown in FIG. 7 is placed on portions at which the hot-melt adhesive is printed as shown in FIG. 6. In this event, the film substrate 10 is positioned such that the wires P1, P2, ..., P10 respectively oppose and contact the wiring layers L1, L2, ..., L10. Thereafter, the hot-melt adhesive is heated at 80 degrees to 150 degrees to be dissolved for adhesion using a small-sized transfer machine, and then is cooled to be cured. This allows the film substrate 10 to adhere to the material 2.

4. Other Embodiments

Figure 8:
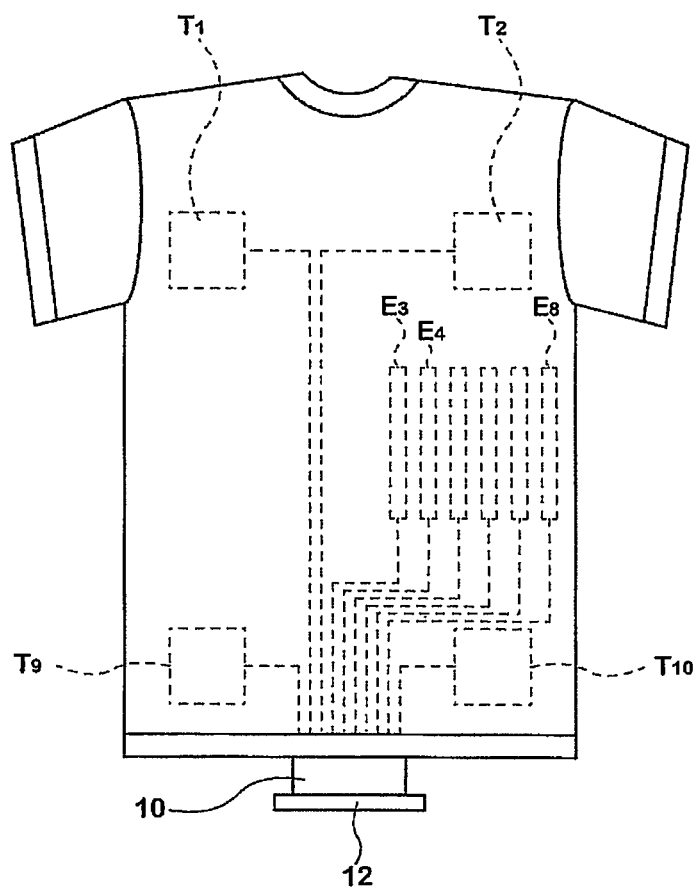
FIG. 8 shows another embodiment.

In the above embodiment, the present invention is implemented as the electrode sheet 1. However, as shown FIG. 8, the chest electrodes E3, E4, ..., E8, the neutral electrodes T1, T2, T9, and T10, and the wiring layers L1, L2, ..., L10 may be provided on the inner side (the side that contacts the skin) of a garment such as a shirt. In the embodiment, preparation for placement of the electrodes for electrocardiogram measurement can be performed by wearing the shirt. The chest electrodes E3, E4, ..., E8 may not be disposed in correct position depending on differences among individual wearers. Thus, in the embodiment, the chest electrodes E3, E4, ..., E8 are elongated vertically as shown in FIG. 8 so as to allow accurate measurement even if the electrodes are displaced.

In the above embodiment, the electrodes are formed from an adhesive material. However, an insulating adhesive may be pasted to desired portions other than the electrodes to improve adhesion of the electrode sheet to a human body.

While the material has the shape of a flat sheet in the above embodiment, the material may have the shape of a thin sheet that conforms to the shape of a body or have the shape of a ring (like a belly band).

In the above embodiment, the material is a woven or knit cloth. However, the material may be a thin flexible sheet made of rubber, plastic, or the like.

EXAMPLES

A material formed by knitting a blended yarn of polyester and urethane was used to measure electrical resistance values. The percentages of polyester fibers and urethane fibers were respectively 82% and 18%.

Figure 10:
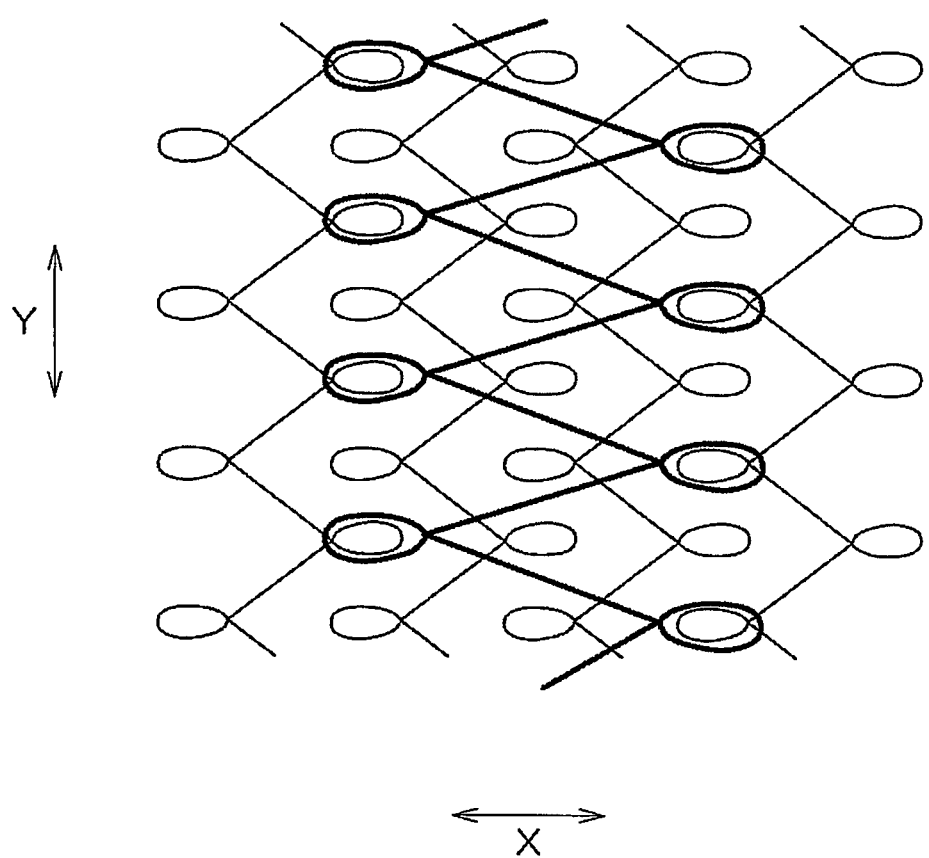
FIG. 10 shows a knitting structure of the material.

FIG. 10 shows a knitting structure of the material. The material was formed of front yarns and back yarns. In the drawing, the front yarns and the back yarns are respectively indicated by the thick lines and the thin lines.

Figure 9:
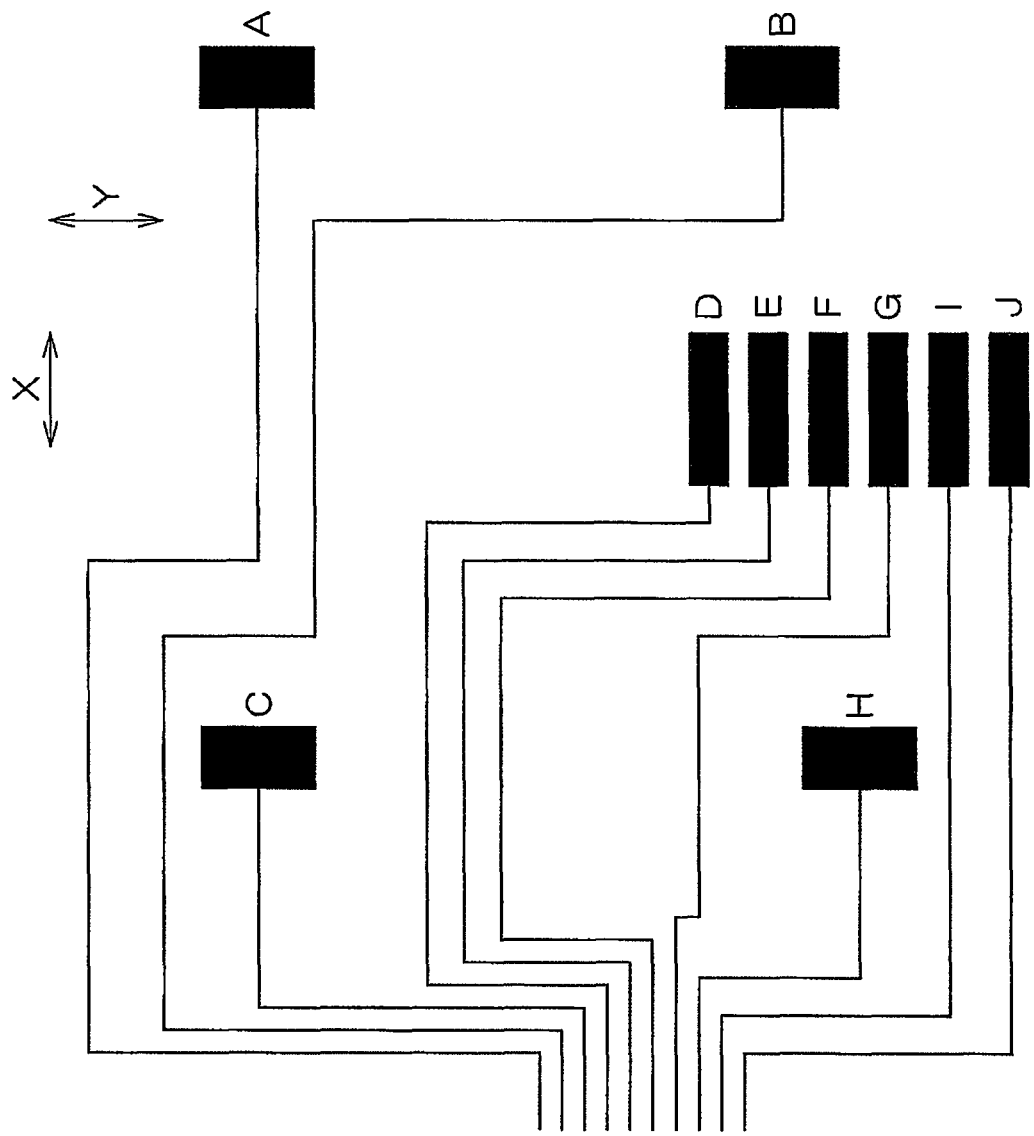
FIG. 9 shows the arrangement of conductive layers that measure electrical resistances.

A lower insulating layer in a pattern as shown in FIG. 9 was printed on the front surface or the back surface of the material, and wiring layers were printed on the lower insulating layer.

An acrylic resin (a binder EN-ME/EN-MRE manufactured by Matsui Shikiso Chemical Co., Ltd.) was used as the insulating ink forming the lower insulating layer. The conductive ink forming the wiring layers was obtained by compounding carbon nanotubes, a dispersant, and a binder. 0.85% (by weight) of an amphipathic acrylic polymer (TX-17-100 manufactured by Kyoeisha Chemical Co., Ltd.) serving as the dispersant, 5.8% (by weight) of an acrylic soft binder (Light Epoch T-23M manufactured by Kyoeisha Chemical Co., Ltd.) serving as the binder, and 5% by weight of multi-layer carbon nanotubes (with a diameter of 150 nm and a length of 10 to 20 μm) were compounded.

In order to verify the effect of smoothing, a comparison was made between a material subjected to a calendering process and a material not subjected to a calendering process.

In the tables below, the "Left" in the "Location" field indicates a measurement performed at the wiring layer connected to the electrode B in FIG. 9. The "Center" indicates a measurement performed at a wiring layer connected to the electrode E. The "Right" indicates a measurement performed at a wiring layer connected to the electrode J. The "Vertical" in the "Knitting direction" field refers to a direction in which the knit yarn is continuous. It corresponds to the Y direction in FIG. 10. The measurements were performed in the Y direction in FIG. 9 corresponding to the vertical knitting direction. The "Horizontal" in the "Knitting direction" field refers to a direction in which the knit yarn is not continuous. It corresponds to the X direction in FIG. 10. The measurements were performed in the X direction in FIG. 9 corresponding to the horizontal knitting direction.

Tables 3 to 6 show measurement values for a case where the calendering process was not performed. Tables 3 and 5 correspond to a case where the wiring layers were printed on the front surface of the material. Tables 4 and 6 correspond to a case where the wiring layers were printed on the back surface of the material. The front surface and the back surface of the material respectively mean a sinker surface and a needle surface.

TABLE 3

Electrical resistance for wiring layers printed on front surface

| Location | Knitting direction | Distance between measurement points (cm) | Electrical resistance | Electrical resistance per cm (kΩ/cm) |
|---|---|---|---|---|
| Left | Vertical | 20 | 120 | 6 |
|  | Horizontal | 10 | 90 | 9 |
| Center | Vertical | 10 | 120 | 12 |
| Right | Vertical | 20 | 150 | 7.5 |
|  | Horizontal | 10 | 150 | 15 |
|  | Average for vertical |  | 130 | 7.8 |
|  | Average for horizontal |  | 120 | 12 |

TABLE 4

Electrical resistance for wiring layers printed on back surface

| Location | Knitting direction | Distance between measurement points (cm) | Electrical resistance | Electrical resistance per cm (kΩ/cm) |
|---|---|---|---|---|
| Left | Vertical | 20 | 40 | 2 |
|  | Horizontal | 10 | 500 or more |  |
| Center | Vertical | 10 | 25 | 2.5 |
| Right | Vertical | 20 | 60 | 3 |
|  | Horizontal | 20 | 500 or more |  |
|  | Average for vertical |  | 41.7 | 2.5 |
|  | Average for horizontal |  | 500 or more |  |

Tables 5 and 6 show the results of measuring a resistance value over the entire length of the wire for each electrode.

TABLE 5

Electrical resistance for all terminals printed on front surface (in kΩ, from left)

| Terminal | Electrical resistance | Average |
|---|---|---|
| A | 300 | 335.0 |
| B | 200 |  |
| C | 300 |  |
| D | 300 |  |
| E | 350 |  |
| F | 350 |  |
| G | 350 |  |
| H | 300 |  |
| I | 500 |  |
| J | 400 |  |

TABLE 6

Electrical resistance for all terminals printed on back surface (in kΩ, from left)

| Terminal | Electrical resistance | Average |
|---|---|---|
| A | 500 or more | 500 or more |
| B | 500 or more |  |
| C | 500 or more |  |
| D | 500 or more |  |
| E | 500 or more |  |
| F | 500 or more |  |
| G | 500 or more |  |
| H | 500 or more |  |
| I | 500 or more |  |
| J | 500 or more |  |

Tables 7 to 10 show measurement values for a case where a calendering process was performed. Tables 7 and 9 correspond to a case where the wiring layers were printed on the front surface of the material. Tables 8 and 10 correspond to a case where the wiring layers were printed on the back surface of the material.

TABLE 7

Electrical resistance for wiring layers printed on front surface

| Location | Knitting direction | Distance between measurement points (cm) | Electrical resistance | Electrical resistance per cm (kΩ/cm) |
|---|---|---|---|---|
| Left | Vertical | 20 | 105 | 5.25 |
|  | Horizontal | 10 | 80 | 8.00 |
| Center | Vertical | 10 | 90 | 9.00 |
| Right | Vertical | 20 | 105 | 5.25 |
|  | Horizontal | 10 | 900 | 9.00 |
|  | Average for vertical |  |  | 5.9 |
|  | Average for horizontal |  |  | 8.5 |

TABLE 8

Electrical resistance for wiring layers printed on back surface

| Location | Knitting direction | Distance between measurement points (cm) | Electrical resistance | Electrical resistance per cm (kΩ/cm) |
|---|---|---|---|---|
| Left | Vertical | 20 | 45 | 2.25 |
|  | Horizontal | 10 | 50 | 5.00 |
| Center | Vertical | 10 | 28 | 2.80 |
| Right | Vertical | 20 | 45 | 2.25 |
|  | Horizontal | 10 | 45 | 4.50 |
|  | Average for vertical |  | 39.3 | 2.4 |
|  | Average for horizontal |  | 47.5 | 4.8 |

Tables 9 and 10 show the results of measuring a resistance value over the entire length of the wire for each electrode.

TABLE 9

Electrical resistance for all terminals printed on front surface (in kΩ, from left)

| Terminal | Electrical resistance | Average |
|---|---|---|
| A | 300 | 245.0 |
| B | 250 |  |
| C | 150 |  |
| D | 150 |  |
| E | 250 |  |
| F | 250 |  |
| G | 200 |  |
| H | 200 |  |
| I | 400 |  |
| J | 400 |  |

TABLE 10

Electrical resistance for all terminals printed on back surface (in kΩ, from left)

| Terminal | Electrical resistance | Average |
|---|---|---|
| A | 105 | 127.5 |
| B | 105 |  |
| C | 100 |  |
| D | 100 |  |
| E | 105 |  |
| F | 105 |  |
| G | 105 |  |
| H | 100 |  |
| I | 250 |  |
| J | 200 |  |

From the above, it can be seen that the conductivity was improved by the calendering process. Moreover, the conductivity was higher in the "vertical" "knitting direction" than the "horizontal" knitting direction, and was higher on the back surface than the front surface. Thus, it is preferable to print the wiring layers using the back surface and such that the direction of the wiring layers matches the vertical knitting direction as much as possible. For example, if the wires as shown in FIG. 9 are formed, it is preferable that the X direction in the drawing corresponds to the "vertical" "knitting direction".

Table 11 shows the results of measuring variations in resistance value in wiring layers in the case where the material was stretched. As the conductive ink, 1.7% (by weight) of an amphipathic acrylic polymer (TX-17-100 manufactured by Kyoeisha Chemical Co., Ltd.) serving as the dispersant, 5.1% (by weight) of an acrylic soft binder (Light Epoch T-23M manufactured by Kyoeisha Chemical Co., Ltd.) serving as the binder, and 9.5% by weight of multi-layer carbon nanotubes (with a diameter of 150 nm and a length of 10 to 20 μm) were compounded.

Wiring layers with a width of 4 mm and a length of 10 cm were formed using the above conductive ink in each of the X direction and the Y direction shown in FIG. 10. Resistance values were measured for the entire length of the wiring layer formed in the X direction in cases where the wiring layer was not stretched, stretched by 30%, and stretched by 50%. The same measurements were performed on the wiring layer formed in the Y direction. The wiring layers were printed after a calendering process was performed on the front surface of the material.

As can be seen from the table, in the case where the wiring layer was stretched by up to about 30%, the resistance value of the wiring layer in either the X direction or the Y direction remained in the order of KΩ. Thus, in view of the fact that the contact resistance of an electrode is several MΩ, such variations in resistance value of the wiring layer are within tolerance and are not practically problematic.

In the case where the wiring layer was stretched by 50%, however, the resistance value of the wiring layer in the X direction was unstable and thus could not be measured although the resistance value of the wiring layer in the Y direction remained in the order of KΩ. Thus, in preparing the electrode sheet 11, it is preferable to match the direction in which the electrode sheet is to be stretched during use with the Y direction of FIG. 10.

TABLE 11

| X direction | |
|---|---|
| Not stretched | 3.16 kΩ |
| Stretched by 30% | 55.4 kΩ |
| Stretched by 50% | — |
| Y direction | |
| Not stretched | 5.71 kΩ |
| Stretched by 30% | 97.3 kΩ |
| Stretched by 50% | 292 kΩ |

Table 12 shows the results of testing the adhesive strength in cases where the material of the film substrate and the component of the hot-melt adhesive were varied. In the tests, an acrylic ester copolymer resin and a nylon resin were used as the component of the hot-melt adhesive, while a polyester film and a polyimide film were used as the material of the film substrate. A thermal transfer machine was used to perform an adhesion process at 150 degrees for 20 seconds.

As is clear from Table 12, the adhesive strength was highest in the case where a polyimide film was used as the film substrate and a nylon resin was used as the hot-melt adhesive.

TABLE 12

| Hot-melt component | Polyester film | Polyimide film |
|---|---|---|
| Acrylic ester copolymer resin | Peel strength: poor | Peel strength: poor |
| Nylon resin | Peel strength: poor | Peel strength: good |

Figure 11:
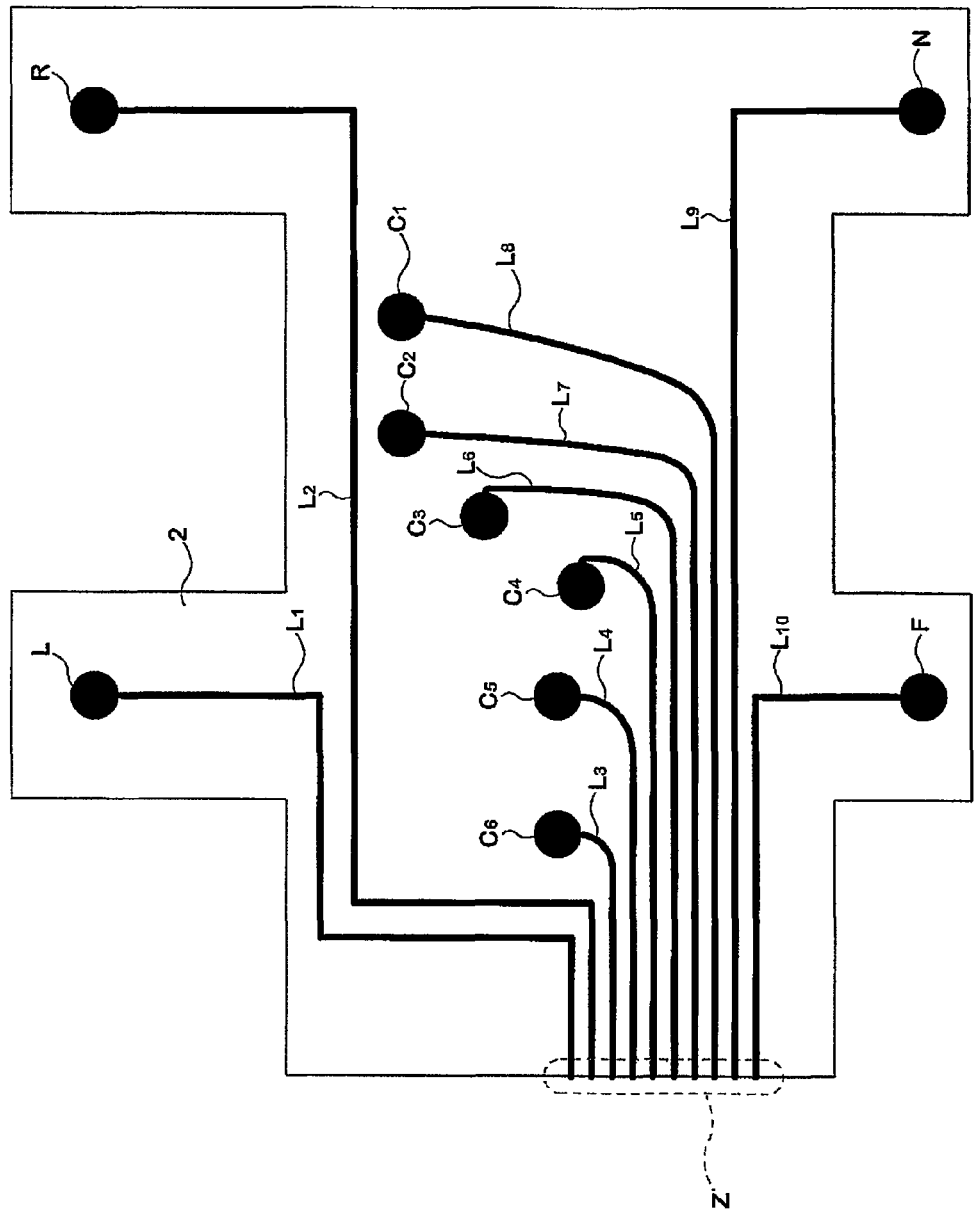
FIG. 11 shows the pattern of conductive layers that measure resistance values.

A lower insulating layer in a pattern as shown in FIG. 11 was printed on a material formed by knitting a blended yarn of polyester and urethane, and wiring layers with a width of 0.4 cm and a thickness of 0.02 to 0.03 cm were printed on the lower insulating layer. The percentages of polyester fibers and urethane fibers were respectively 82% and 18%.

An acrylic resin (a binder EN-ME/EN-MRE manufactured by Matsui Shikiso Chemical Co., Ltd.) was used as the insulating ink forming the lower insulating layer. The conductive ink forming the wiring layers was obtained by compounding carbon nanotubes, a dispersant, and a binder. 1.7% (by weight) of an amphipathic acrylic polymer (TX-17-100 manufactured by Kyoeisha Chemical Co., Ltd.) serving as the dispersant, 5.1% (by weight) of an acrylic soft binder (Light Epoch T-23M manufactured by Kyoeisha Chemical Co., Ltd.) serving as the binder, and 9.5% by weight of multi-layer carbon nanotubes (with a diameter of 150 nm and a length of 10 to 20 μm) were compounded. A calendering process was performed.

Table 13 shows the results of measuring resistance values between electrodes L, R, F, N, and C1 to C6 and starting points Z of respective wires corresponding to the electrodes in cases where the conductive ink forming the wiring layers were printed once, and twice, three times, four times, and five times at the same position in an overlapping manner. The distances to the electrodes from the respective starting points were as follows.

|  |  |
|---|---|
| L: | 33.5 |
| R: | 62.0 |
| C6: | 7.5 |
| C5: | 12.5 |
| C4: | 23.5 |
| C3: | 26.5 |
| C2: | 29.5 |
| C1: | 35.0 |
| N: | 45.5 |
| F: | 20.0 |

TABLE 13

|  | Printed once | Printed twice | Printed three times | Printed four times | Printed five times |
|---|---|---|---|---|---|
| L | 46.3 | 22.9 | 19.3 | 18.8 | 13.6 |
| R | 79.8 | 30.8 | 24.6 | 24.5 | 20.0 |
| C6 | 6.5 | 2.8 | 1.7 | 1.3 | 1.1 |
| C5 | 12.4 | 4.3 | 3.6 | 2.0 | 2.4 |
| C4 | 19.5 | 6.7 | 4.6 | 3.4 | 3.3 |
| C3 | 29.2 | 9.9 | 8.0 | 6.6 | 5.5 |
| C2 | 35.3 | 13.1 | 12.2 | 11.5 | 8.9 |
| C1 | 40.0 | 15.0 | 13.2 | 13.7 | 10.6 |
| N | 58.5 | 18.0 | 14.1 | 11.9 | 9.1 |
| F | 25.0 | 12.2 | 7.4 | 7.3 | 4.2 |
| Average | 35.25 | 13.56 | 10.87 | 10.10 | 7.87 |

The symbols representing the electrodes in the table correspond to the symbols in FIG. 11. It should be noted that the conductivity was drastically enhanced by printing the wiring layers twice.

Table 14 shows the comparison results of resistance values between cases where wiring layers with a width of 0.4 cm, a thickness of 0.02 to 0.03 cm, and a length of each of 10 cm and 20 cm were printed once, twice, three times, four times, and five times under the same conditions as described above, and between cases where wiring layers with a width of 1.0 cm, a thickness of 0.02 to 0.03 cm, and a length of each of 10 cm and 20 cm were printed once, twice, and three times under the same conditions as described above.

TABLE 14

| Conductor width: 1.0 cm | | | |
|---|---|---|---|
| CNT Length | Ink printed once | Ink printed twice | Ink printed three times |
| 10 cm | 6.0 | 1.6 | 1.2 |
| 20 cm | 13.1 | 3.1 | 2.0 |

| Conductor width: 0.4 cm | | | | | |
|---|---|---|---|---|---|
| CNT Length | Ink printed once | Ink printed twice | Ink printed three times | Ink printed four times | Ink printed five times |
| 10 cm | 10.2 | 5.1 | 3.0 | 1.9 | 1.6 |
| 20 cm | 21.7 | 9.1 | 5.3 | 3.2 | 3.1 |

According to the table, the resistance values were approximately the same between the case where the wiring layers with a width of 0.4 cm were printed four times and the case where the wiring layers with a width of 1.0 cm were printed twice. Thus, it was found that the number of printing in an overlapping manner can be reduced by increasing the width of the wiring layers.

What is claimed is:

1. A process for making an electrode sheet, comprising the steps of:
   providing a material, the material being formed by knitting or weaving;
   flattening at least one surface of the material that was formed by knitting or weaving;
   printing a conductive ink containing carbon nanotubes on the one flattened surface of the material to form a wiring layer; and
   forming, on the electrode sheet, an electrode electrically connected to the wiring layer, the wiring layer extending from the electrode to an edge of the electrode sheet.

2. The process of making an electrode sheet according to claim 1,
   wherein the conductive ink contains a binder containing an acrylic resin, a dispersant containing an acrylic acid polymer, and carbon nanotubes.

3. The process of making an electrode sheet according to claim 1,
   wherein the material is produced by knitting or weaving, and is selected from group consisting of: a blended yarn of polyester fibers and urethane fibers, a yarn of nylon fibers, and a yarn of urethane fibers.

4. The process of making an electrode sheet according to claim 1,
   wherein the material is flattened by a calendering process.

5. The process for an electrode sheet according to claim 1,
   wherein after the material is flattened,
   a non-conductive ink is printed on the one flattened surface of the material to form a lower insulating layer, and
   the wiring layer is formed on the lower insulating layer.

6. The process of making an electrode sheet according to claim 1,
   wherein after the wiring layer is formed,
   an insulating ink is printed on the wiring layer to form an upper insulating layer.

7. The process of making an electrode sheet according to claim 1,
   wherein an adhesive conductive paste is applied on the wiring layer to form the electrode.

8. The process of making an electrode sheet according to claim 1, wherein the electrode is an electrode that measures an electrocardiographic waveform of a wearer of the electrode sheet.

9. The process of making an electrode sheet according to claim 1,
wherein the wiring layer and a wire on a film substrate connected to a connector are secured by a hot-melt adhesive.

\* \* \* \* \*